United States Patent [19]
Thiede et al.

[11] Patent Number: 5,965,436
[45] Date of Patent: Oct. 12, 1999

[54] METHOD OF ISOLATING MESENCHYMAL STEM CELLS ASSOCIATED WITH ISOLATED MEGAKARYOCYTES BY ISOLATING MEGAKARYOCYTES

[75] Inventors: Mark A. Thiede, Forest Hills; Daniel R. Marshak, Lutherville, both of Md.

[73] Assignee: Osiris Therapeutics, Inc., Baltimore, Md.

[21] Appl. No.: 08/969,260

[22] Filed: Nov. 13, 1997

Related U.S. Application Data

[60] Provisional application No. 60/030,953, Nov. 15, 1996.
[51] Int. Cl.[6] .............................. C12N 5/08; A01N 63/00
[52] U.S. Cl. ......................... 435/372; 435/366; 424/93.7
[58] Field of Search ..................................... 435/325, 366, 435/372; 424/93.7

[56] References Cited

U.S. PATENT DOCUMENTS

| 5,340,719 | 8/1994 | Hajek et al. | 435/7.21 |
|---|---|---|---|
| 5,486,359 | 1/1996 | Caplan et al. | 424/93.7 |

OTHER PUBLICATIONS

Rabellino et al., "Human Megakaryocytes", J.Exp. Med. Jun. 1979, vol. 149, pp. 1273–1287.
Grant et al., "A radioimmunoassay useful fro quatitating megakaryocyre growth in vitro", In:Megakaryocyte Development and Function, ED. Levine et al., 1986 Alan R.Liss, Inc., pp. 117–121.
Hoffman et al., "Regulation of Megakaryocytopoisis", Blood, 1989, vol. 74, No. 4, pp. 1196–1212.
Tanaka et al., "Isolation of human megakaryocyes by immunomagnetic beads", British Jouranl of hematology, 1989, 73, 18–22.

*Primary Examiner*—Sandra E. Saucier
*Assistant Examiner*—Vera Afremova
*Attorney, Agent, or Firm*—Elliot M. Olstein; Raina Semionow

[57] ABSTRACT

The present invention is directed to isolated and purified human mesenchymal stem cells, to a method for isolating, purifying, and culturally expanding human mesenchymal stem cells (i.e. mesenchymal stem cells or "MSCs"), and to the characterization of and uses for such cells. In particular, the invention relates to isolation of MSCs that are associated with hematopoietic cells, such as megakaryocyte precursors, in the bone marrow.

15 Claims, 7 Drawing Sheets

Anti CD41 Mab

Magnet

METHOD OF ISOLATING MESENCHYMAL STEM CELLS ASSOCIATED WITH ISOLATED MEGAKARYOCYTES BY ISOLATING MEGAKARYOCYTES

This application claims the priority of U.S. Provisional Application Serial No. 60/030,953 filed Nov. 15, 1996.

The present invention is directed to the isolation of human mesenchymal stem cells ("MSCs") and to recovering mixed populations of MSCs and megakaryocytes.

BACKGROUND OF THE INVENTION

Mesenchymal stem cells are the formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines. Although these cells are normally present at very low frequencies in bone marrow, the inventors of the present invention have discovered a process for isolating, purifying, and greatly replicating these cells in culture, i.e. in vitro.

The production of hematopoietic cytokines and growth factors by cultured MSCs shows that MSCs support the formation of hematopoietic colonies in co-culture with CD34+ hematopoietic megakaryocytes. Of particular interest to the field of bone marrow transplantation is the role that MSCs may play in the proliferation and differentiation of myeloid precursor cells such as those for megakaryocytes. This could lead to a better understanding of the development of megakaryocytes, which is important since the time to platelet recovery following bone marrow or peripheral blood progenitor transplantation can be very protracted. Cultured MSCs produce GM-CSF, IL-6, IL-11 and thrombopoietin (TPO), cytokines which have been shown to be important for both megakaryocyte and plate production, which is evidence that MSCs function in megakrayocytopoiesis and thrombocytopoiesis. Another link between MSC proliferation and platelet development is that platelet-derived growth factor (PDGF) and serotonin are two major products secreted by platelet that are important to MSC proliferation.

In one aspect, the present invention is directed to human mesenchymal stem cells isolated from a tissue specimen, such as marrow cells, and to the method of their isolation involving separating from the specimen MSCs associated with hematopoietic progenitor cells (such as megakaryocytes). In such a separation process, at least one antibody specific for surface antigens on the megakaryocytes rather than for antigens on MSCs are utilized to obtain an enriched or substantially pure culture of megakaryocytes which have associated therewith MSCs. The MSCs may be recovered by culturing the associated cells under conditions which favor the growth and proliferation of MSCs.

Figure 1:
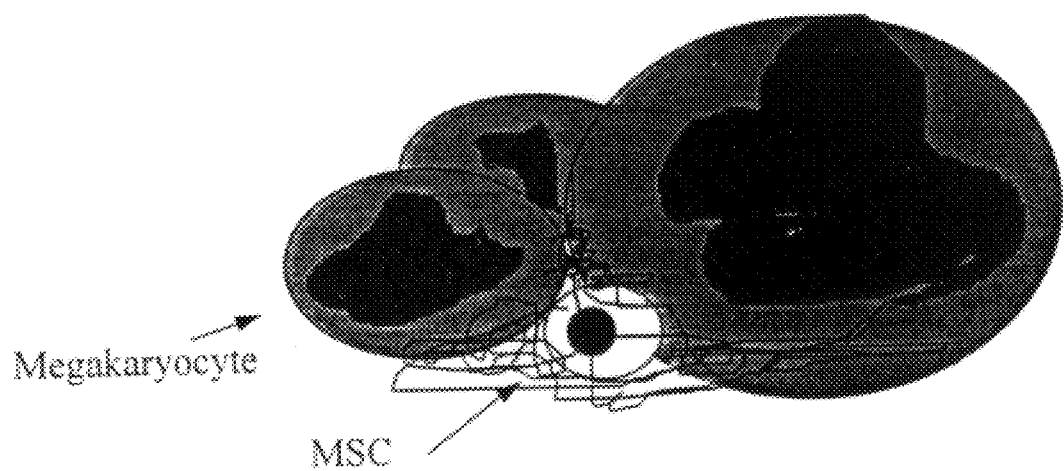
FIG. 1 illustrates a model of MSC Megakaryocyte interaction which shows the MSCs located within a group of the much larger megakaryocytes. A certain number of MSCs become associated in a sample with the megakaryocytes.
Figure 2A:
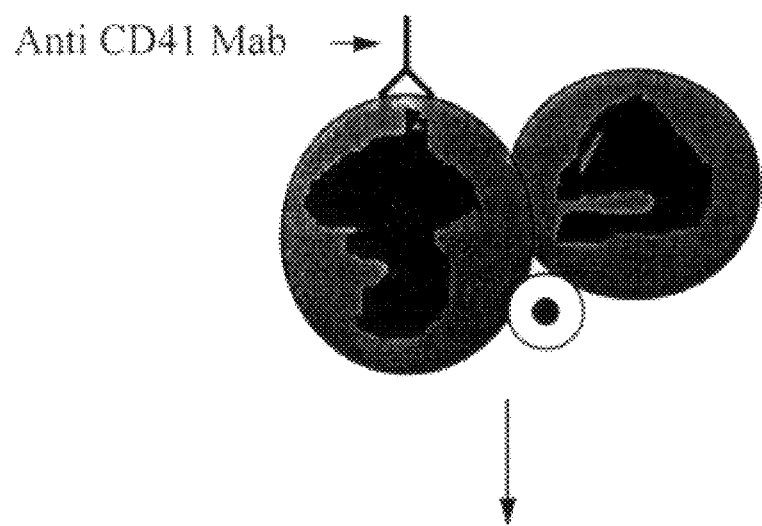
FIG. 2A shows how an antibody (anti-CD41 monoclonal antibody), or polyclonal antibody, can become attached to an antigen on the surface of a megakaryocyte. As illustrated, the group or clump of megakaryocytes and the associated MSC in the "clump" are all then attached to the antibody via the antigen on the surface of one of the megakaryocytes of the clump.
Figure 2B:
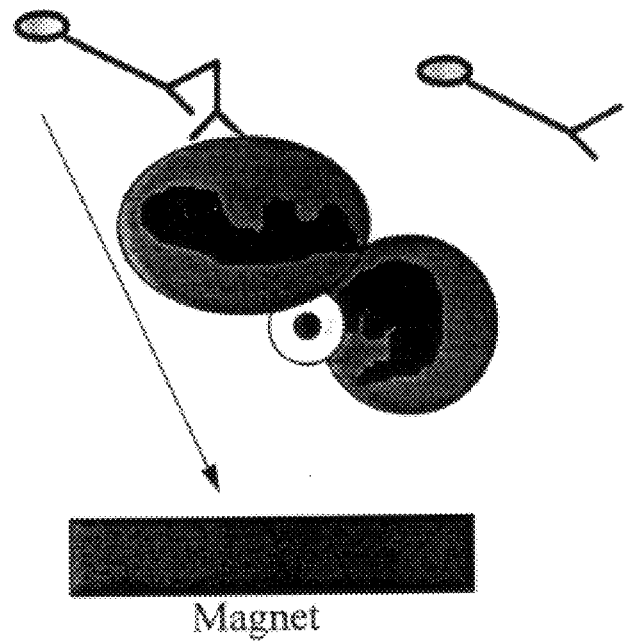
FIG. 2B shows how an antibody which is attached to a bead such as a magnetic bead can be utilized to isolate the clump which has become attached to the antibody/magnetic bead complex by utilizing a magnet. After sufficient amount of time has passed for a magnetic bead/antibody complex to become attached to the surface antigens on the megakaryocytes in a solution the solution is passed by a magnet and then drained to leave the complexes attached to the magnet.
Figure 3:
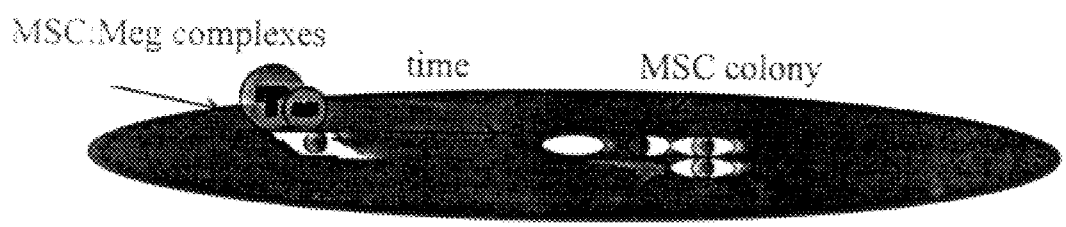
FIG. 3 shows how a megakaryocyte MSC complex which has been separated from a sample solution is placed upon a culture plate of an appropriate culture medium for a period of time to proliferate and grow into a MSC colony.

Homogeneous human mesenchymal stem cell compositions are provided which serve as the progenitors for all mesenchymal cell lineages. The presence of MSCs in the culture colonies may be verified by specific cell surface markers which are identified with unique monoclonal antibodies, for example, see U.S. Pat. No. 4,586,359. Such homogeneous compositions may be obtained by isolating MSCs from the recovered megakaryocyte population. These isolated mesenchymal cell populations display epitopic characteristics associated with only mesenchymal stem cells, have the ability to regenerate in culture without differentiating, and have the ability to differentiate into specific mesenchymal lineages when either induced in vitro or placed in vivo at the site of damaged tissue.

The present invention relates generally to recovering megakaryocytes from a human followed by the separation and recovery of MSCs associated with such megakaryocytes. Applicants have found that MSCs are in association with megakaryocytes in tissue and that it is possible to recover from a human the megakaryocytes along with their associated MSCs and then optionally to isolate the MSCs that were in association with the recovered megakaryocytes. Thus, in accordance with the present invention it is possible to recover and utilize a population rich in megakaryocytes and MSCs, or subsequently to isolate MSCs from the population.

Accordingly, any process that is useful to recover megakaryocytes from human tissue may be utilized to result in a population of cells having megakaryocytes and associated MSCs In order to obtain subject human mesenchymal stem cells by a process according to the invention, it is necessary to isolate rare pluripotent mesenchymal stem cells that are associated with megakaryocytes, by isolating megakaryocytes from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood.

In one aspect, the method of their isolation comprises the steps of providing a tissue specimen containing mesenchymal stem cells, isolating megakaryocytes having associated MSCs from the specimen, adding the megakaryocyte cells with associated MSC cells from the tissue specimen to a medium which contains factors that stimulate mesenchymal stem cell growth without differentiation and allows, when cultured, for the selective adherence of only the mesenchymal stem cells to a substrate surface, culturing the specimen-medium mixture, and removing the non-adherent matter from the substrate surface.

In particular, the invention relates to isolation of MSCs that are associated with megakaryocyte precursors in the bone marrow by utilizing antibodies against megakaryocyte and platelet specific antigens to isolate megakaryocyte rich compositions from bone marrow, which upon culturing will yield MSCs that were associated with the isolated megakaryocyte-rich compositions.

Further, the present invention is directed to a process which recovers megakaryocytes from human tissue along with MSCs associated with those megakaryocytes, and optionally isolating the MSCs from the mixture. One such recovery process utilizes antibodies (such as monoclonal antibodies) that are specific for cell surface antigens (e.g., CD41, 34, etc.) on hematopoietic cells to select specific hematopoietic cells from a marrow cell suspension and obtain a percentage of MSCs that reside in contact with them. Such antibodies will not interact directly with MSCs, but will bind to the surface of another hematopoietic cell such as a megakaryocyte. Following collection of the antibody:cell complexes, the complexes may be cultured in media which will favor the growth of MSCs. Thus, colonies of MSCs are formed in the culture from MSCs that were adhered to the other hematopoietic cells.

Human mesenchymal stem cells produced by the method according to the present invention may be used for therapeutic and/or diagnostic purposes. For example, human mesenchymal stem cells find use in: (1) regenerating mesenchymal tissues which have been damaged through acute injury, abnormal genetic expression or acquired disease; (2) treating a host with damaged mesenchymal tissue by removal of small aliquots of bone marrow, isolation of their mesenchymal stem cells and treatment of damaged tissue with culture-expanded MSCs combined with a biocompatible carrier suitable for delivering MSCs to the damaged tissues site(s); (3) producing various mesenchymal tissues; (4) detecting and evaluating growth factors relevant to MSC self-regeneration and differentiation into committed mesenchymal lineages; (5) detecting and evaluating inhibitory factors which modulate MSC commitment and differentiation into specific mesenchymal lineages; and (6) developing mesenchymal cell lineages and assaying for factors associated with mesenchymal tissue development.

The present invention relates to the discovery that megakaryocytes can be recovered from various types of tissue such as bone marrow, blood (including peripheral blood), periosteum and dermis, and other tissues which have mesodermal origins. Although human mesenchymal stem cells or "MSCs" are normally present in bone marrow, for example, in very minute amounts and these amounts greatly decrease with age (i.e. from about 1/10,000 cells in a relatively young patient to as few as 1/2,000,000 in an elderly patient), such human mesenchymal stem cells can be recovered in association with the recovered megakaryocytes. The MSCs may then be recovered from the mixed population comprising megakaryocytes and MSCs by techniques known in the art which favor expansion of MSCs without differentiation, e.g., as described in U.S. Pat. No. 5,486,359.

Relative to the MSCs isolated using a Percoll solution of density 1.073 gm/ml, MSCs are enriched in the fraction of marrow cells that sediment at density $\leq 1.050$ gm/ml in Percoll. This low density fraction contains about 1% of the total marrow cells and approximately 25% of the MSC colony forming units of the bone marrow. This fraction is also highly enriched in megakaryocytes, the large hematopoietic bone marrow cells that produce platelets.

The table below presents data regarding utilization of differing density Percoll media for isolation of the cells:

| Percoll density Enrichment | % of total cells loaded onto Percoll | Enrichment vs 1.073 gm/ml | cells | CFU-f/$10^5$ |
| --- | --- | --- | --- | --- |
| 1.045 gm/ml | 1.1% | 20 | 265 +/− 194 | 5.7 |
| 1.050 gm/ml | 1.1% | 20 | 299 +/− 223 | 6.5 |
| 1.055 gm/ml | 1.9% | 11 | 245 +/− 158 | 5.3 |
| 1.073 gm/ml | 22.4 | — | 46 +/− 12 | — |

Usually greater than 95% of the CFU-f of the marrow can be recovered at the interface of the 1.073 gm/ml Percoll. If it is assumed that 100% of the CFU-f are recovered in the 1.073 fractions, the percentage of the total CFU-f recovered in the 1.045, 1.050 and 1.055 gm/ml would be in the range of 25–30%.

Figure 4:
FIG. 4 A MSC and megakaryocyte complex isolated from canine bone marrow using a Percoll solution of density 1.045 gm/ml. Note the spindle-shaped adherent cells (MSCs) growing out from a cluster of megakaryocytes (arrows). Magnification=40×.
Figure 5:
FIG. 5 Formation of bone (arrow) in ceramic cubes implanted with MSCs isolated from the 1.055 gm/ml fraction of bone marrow. Similar histology was observed in cubes loaded with cells grown from the 1.045, 1.050 and 1.073 gm/ml fraction of marrow. Magnification=40×

Microscopic analysis of the 1.045, 1.050 or 1.055 gm/ml fractions will reveal the presence of platelets, small mononuclear cells and a relatively high density of large cells (megakaryocytes) and clumps of cells. Two days after initial plating, spindle-shaped cells will appear with the adherent clusters (such as in FIG. 4) and with time these cells will eventually develop into colonies with the characteristic whorled morphology. Large megakaryocytes (large spherical cells) and small hematopoietic cells can be found attached to the small adherent colony indicating that a physical association between hematopoietic cells including megakaryocytes.

Figure 6:
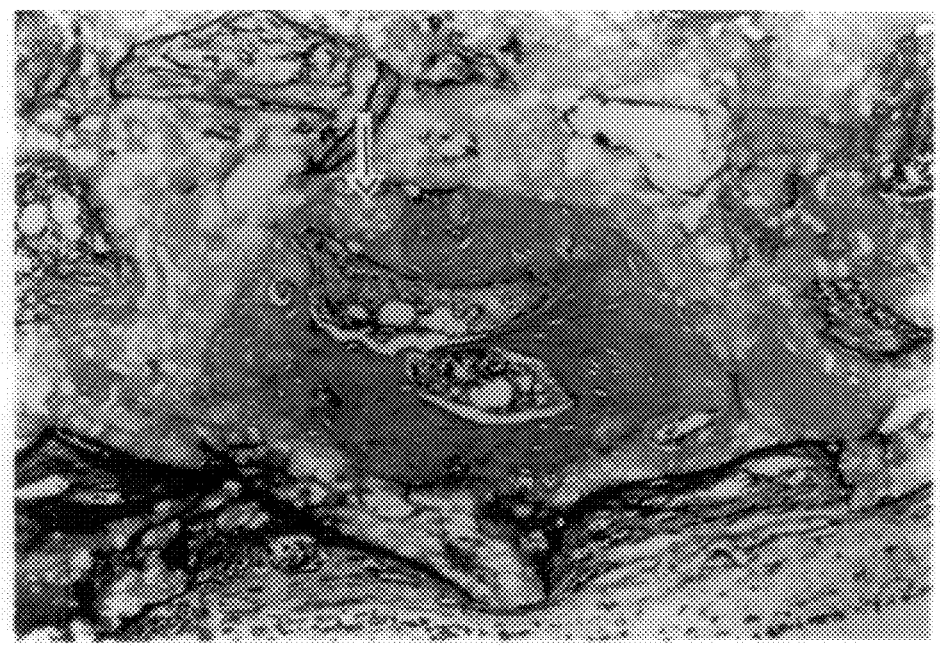
FIG. 6 Formation of bone and cartilage (arrow) in ceramic cubes implanted with MSCs isolated from the 1.055 gm/ml fraction of bone marrow. Similar histology was observed in cubes loaded with cells grown from the 1.045, 1.050 and 1.073 gm/ml fraction of marrow. Magnification=40×
Figure 7:
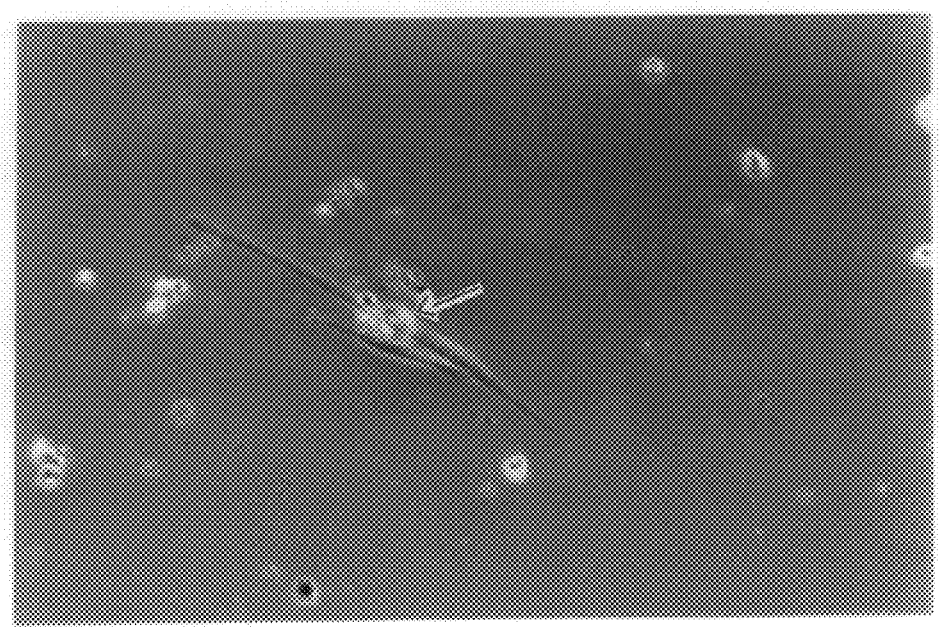
FIG. 7 Presence of early MSC colony in a culture of CD41+ selected cells 3 days post-plating in human MSC media. The CD41+ cells with Dynabeads on their surface are highlighted with an arrow. Magnification=100×.

Cells that propagate from colonies isolated in the 1.045, 1.050 or 1.055 gm/ml fractions can be expanded in culture. Samples of these cells can be loaded into fibronectin-coated cubes of hydroxy apatite, and subsequently the cubes can be implanted subcutaneously into nude mice. In about 6 weeks after such implantation the cubes can be removed for histological analysis. As shown in FIGS. 6 and 7, pores of the cubes will contain both bone and cartilage. Such data would indicate that cells isolated with the megakaryocyte-rich, low density cell fraction of bone marrow form adherent colonies that are composed of cells that have multipotential in vivo.

Since MSCs are in physical association with a portion of the megakaryocytes in the megakaryocyte-rich fraction antibodies against megakaryocyte surface antigens may be utilized to recover the clumps, such as CD41 or CD61 antibodies, which are available commercially. For example, such antibodies may be conjugated to magnetic beads and immunomagnetic procedures utilized to separate the clumps from the fraction.

The isolated clumps may be cultured by methods which favor MSC growth, which adhere to the surface of the culture plate and may be separated from the non-adherent megakaryocytes. A homogeneous population of MSCs may be thus obtained.

Compositions having greater than 95% usually greater than 98% of human mesenchymal stem cells can be obtained by proceeding in accordance with the invention. The desired cells in such compositions are identified as $SH2.^+$, $SH3.^+$, $SH4.^+$ and CD.sup.- and are able to provide for both self renewal and differentiation into the various mesenchymal lineages. The characteristics of such cells are described in U.S. Pat. No. 5,486,359.

Since the MSC which are in association with megakaryocytes may be difficult for antibodies specific for the MSCs to reach and attach the MSCs, a multi-step procedure may be utilized to recover the MSCs by direct attachment with specific antibodies (such as the monoclonal antibodies of ATCC HB 10743, ATCC HB 10744 or ATCC HB 10745 as described in U.S. Pat. No. 5,486,359) in combination with the above described indirect recovery method of isolating clumps that have the MSCs imbedded therein.

In accordance with another aspect of the present invention, megakaryocytes are recovered from tissue derived from a human, and such megakaryocytes are subsequently used to provide a source of human mesenchymal stem cells.

In accordance with this aspect of the invention, the megakaryocytes as a result of being human mesenchymal stem cells associated therewith and used as a source of human mesenchymal stem cells for therapeutic application, without separating the human mesenchymal stem cells from the megakaryocytes. Thus, the mixed population may be used for the purposes for which isolated mesenchymal stem cells are used.

Perhaps the most obvious clinical use for the uncultured mixed population of megakaryocytes and MSCs is treating a cancer population. Infusion of freshly harvested CD41-cell:MSC complexes amy be utilized to supplement hematopoietic stem cell transplants. The combination of these complexes with CD34+ cells would shorten platelet recovery following myeloablative therapy, while providing MSCs. Further, cDNA libraries may be obtained from such complexes to isolate unique molecules involved in the MSC megakaryocyte interactions.

Although, megakaryocyte/MSC complexes may be obtained directly from unfractioned marrow, it is preferred to utilize the above described procedures. Platelet contamination and red blood cell contamination in the marrow should be dealt with. Low speed centrifugation of Percoll fractionated cells is a preferred way to eliminate the majority. Fractionation on Ficoll or other separation media also be utilized.

A typical Percoll Fractionation may generally described as follows:

(1) Transfer fresh marrow aspirate to a sterile vessel and add an equal volume of C-HBS;
(2) Centrifuge at about 1000×g for 10 minutes recover cells. (Measure volume of cell pellets and determine number of mononuclear cells/ml);
(3) Dilute cells with Citrated-Hank's BS to a final concentration of $20 \times 10^6$ cells/ml and carefully layer 10 ml of the cell suspension onto 20 mls of a 1.073 gm/ml Percoll;
(4) Centrifuge at 400×g for 35 minutes. Do not use a brake to stop centrifugation.
(5) Recover cells at the media:Percoll interface and dilute cells with 2 volumes C-HBS, centrifuge at ≧200×g for 10 min to recover cells. Discard the platelet-rich supernatant.
(6) Resuspend cells in CATCH buffer and count cells.
(7) Plate $30 \times 10^6$ in a 185 $cm^2$ flask. (about 100,000 cells/$cm^2$)
(8) Place aliquots of Percoll fractionated cells in a sterile tubes.

A typical isolation of megakaryocyte/MSC clumps with an antibody may be generally described as follows:

(1) Anti-CD41 antibodies are utilized, for example.
(2) The antibodies are incubated with the fraction for about 30 min at about 4° C. with shaking;
(3) During the 30 minute incubation, anti-mouse IgG-Dyna beads may be prepared for addition to the cells by washing the beads with CATCH buffer. Dynabeads may be utilized for each 20 million cells aliquot of Percoll fractionated cells. The washed beads may be collected by placing the tube next to a magnet;
(4) Using more that 5 ml of beads would not usually increase efficiency of recovery but may increase background. The washed Dynabeads may be resuspended in CATCH buffer using about 0.5 ml for every 20 million cells used;
(5) The cells may be recovered following incubation with primary antibody by centrifuging the tube at 1000×g for 5 minutes;
(6) optionally the cells are resuspended in 2 ml of CATCH and centrifugation is repeated;
(7) Preferably, after resuspending the cells in CATCH buffer containing washed Dynabeads as described above, the cell/bead combination can be placed in a tightly sealed tube and agitated continuously for 90 minutes at 4° C. on a labquake rotating device to prevent the cells from settling to the bottom;
(8) The attached cells ("selected cells") may be recovered on a magnet and the unselected cells should be transferred to a new tube.
(9) The cells may be washed and resuspended as needed to disperse aggregates and recover the beads and cells on the magnet.

Recovered cell fraction clumps are evaluated for the presence of MSCs by culturing and assaying for the presence of MSC.

EXAMPLE 1

Immuno-selection of MSCs from Human Bone Marrow.

A. Marrow Samples

MSCs were immuno-selected from human bone marrow by utilizing anti-CD41 mAb. From 20–40 million cells were utilized for each selection and the anti-CD41 antibody was added at 1 mg of anti-CD41 per 5 million mononuclear cells. The CD41 mAb was obtained from Immunotech. The lyphylized antibody was resuspended in 1 ml o sterile H2) and 25 ml (5 mg) aliquots are stored at 70° C.

Marrow samples capable of yielding about 20–40 million cells were obtained and sodium citrate 4 gm/l was added to Hanks's buffer saline to minimize the activation of platelets in the marrow samples and to provide a Catch buffer solution.

B. Catch Buffer

Cell collected by Percoll fractionation as described above will be resuspended in Catch buffer to minimize the chance for platelet and megakaryocyte activation. The Catch buffer solution utilized had the following composition:

CATCH Buffer—Composition

| Final concentration | gm/liter |
|---|---|
| 13.6 mM Na citrate | 3.99 |
| 11.1 mM glucose | 2.00 |
| 1.0 mM adenosine | 0.267 |
| 1.0 mM theophylline | 0.180 |
| 10 mM HEPES | 10 ml of a 1 M stock |
| 0.5% BSA | 5.00 |
| 0.15 U/ml Apyrase | add 1 ul of a 1.5 U/ml/ 10 ml CATCH just prior to use |
| 1 U/ml Hirudin | add to CATCH just prior to use. |

C. Percoll Procedure

Fresh marrow aspirate was transferred to a sterile vessel and an equal volume of C-HBS was added. The mixture was centrifuged at about 1000×g for 10 minutes to recover the cells. The volume of the cell pellets was measured and the number of mononuclear cells/ml was determined. The cells were diluted with Citrated-Hank's BS to a final concentration of $20 \times 10^6$ cells/ml and carefully layer 10 ml of the cell suspension onto 20 mls of a 1.073 gm/ml Percoll. This dilution was centrifuged at 400×g for 35 minutes. No brake was used to stop the centrifugation.

Cells were recovered at the media:Percoll interface, diluted with 2 volumes C-HBS, and centrifuged at ≧200×g for 10 min to recover cells. The platelet-rich supernatant was discarded. The cells were resuspended in CATCH buffer and counted. The cells were plated $30 \times 10^6$ in a 185 cm² flask (about 100,000 cells/cm²).

Aliquots of Percoll fractionated cells were placed in sterile tubes for separation procedures utilizing antibodies.

D. Antibody Separation of MSCs in Association with Megakaryocytes

The resuspended CD41 antibodies described above were incubated with the Percoll fraction for about 30 min at about 4° C. with shaking of the tube. During the 30 minute incubation, anti-mouse IgG-Dyna beads were prepared for addition to the cells by washing the beads with CATCH buffer. Dynabeads were utilized for each 20 million cells aliquot of Percoll fractionated cells. The washed beads were collected by placing the tube next to a magnet. The washed Dynabeads were resuspended in CATCH buffer using about 0.5 ml for every 20 million cells. The cells were recovered from the buffer solution following incubation with primary antibody by centrifuging the tube at 1000×g for 5 minutes. The cells were twice more resuspended in 2 ml of CATCH and centrifugation repeated. After resuspending the cells in CATCH buffer containing washed Dynabeads as described above, the cell/bead combination was placed in a tightly sealed tube and agitated continuously for 90 minutes at 4° C. on a labquake rotating device to prevent the cells from settling to the bottom.

The attached cells ("selected cells") were recovered on a magnet and the unselected cells were transferred to a new tube. The cells were washed and resuspended sufficiently to disperse aggregates and recover the beads and cells on the magnet.

E. Evaluation of Attached Cells by Culturing.

An aliquot of the selected cells were plated into plastic dishes and cultured in the presence of human MSC media. The media was changed 2 days after initial plating and every 3–4 days thereafter. The cultures were watched for the first signs of MSC outgrowth. The first evidence of spindle shaped adherent cells was observed on around the third day (see FIG. 7). You will note in FIG. 7 that the Dynabeads were not found on the adherent cells. Using flow cytometry, it was determined that MSCs were negative for CD41.

Figure 8:
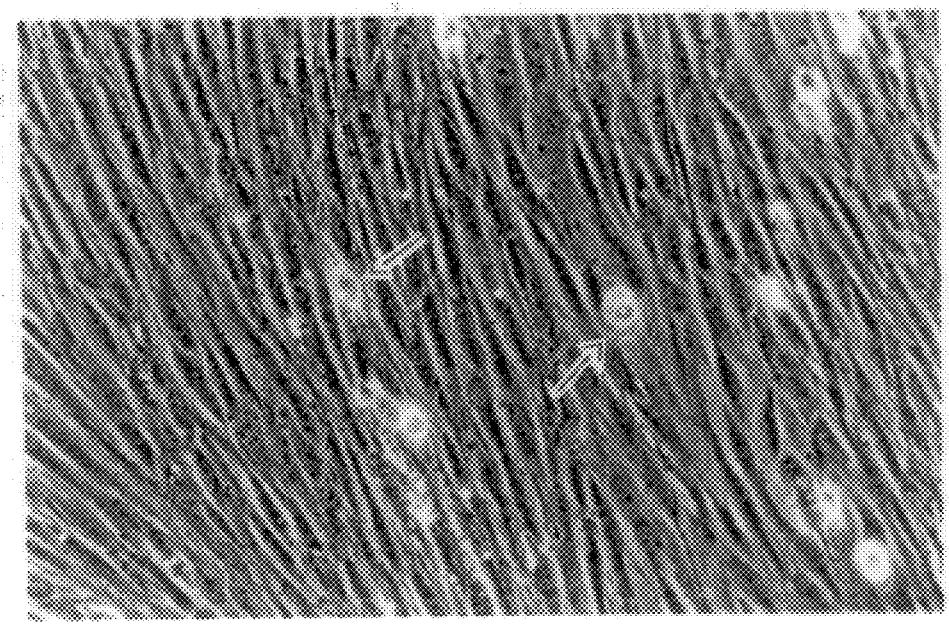
FIG. 8 Culture of CD41+ cells 13 days after plating in human MSC media. CD41+ cells with Dynabeads on their surface are highlighted with an arrow. Magnification=100×

As seen in FIG. 8, CD41 positive cells (seen with Dynabeads on their surfaces) were associated with MSCs within colonies after 13 days of culture. Since the culture conditions were not appropriate for in vitro megakaryocytopoiesis, the CD41+ cells did not proliferate during such a time period.

Figure 9:
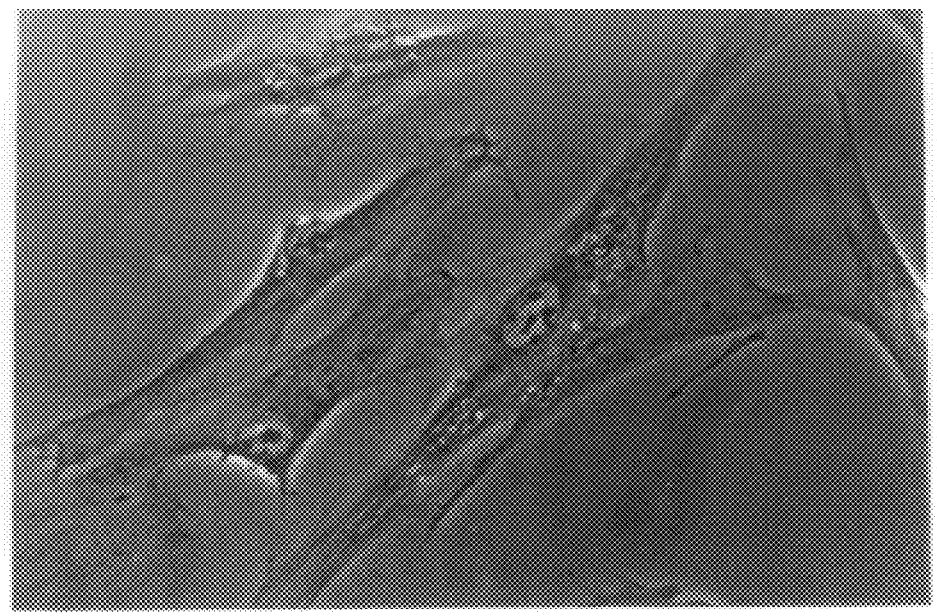
FIG. 9 Phase-contrast photomicrograph of cells that propagated from a culture of human CD41-selected cells. Magnification=400×
Figure 10:
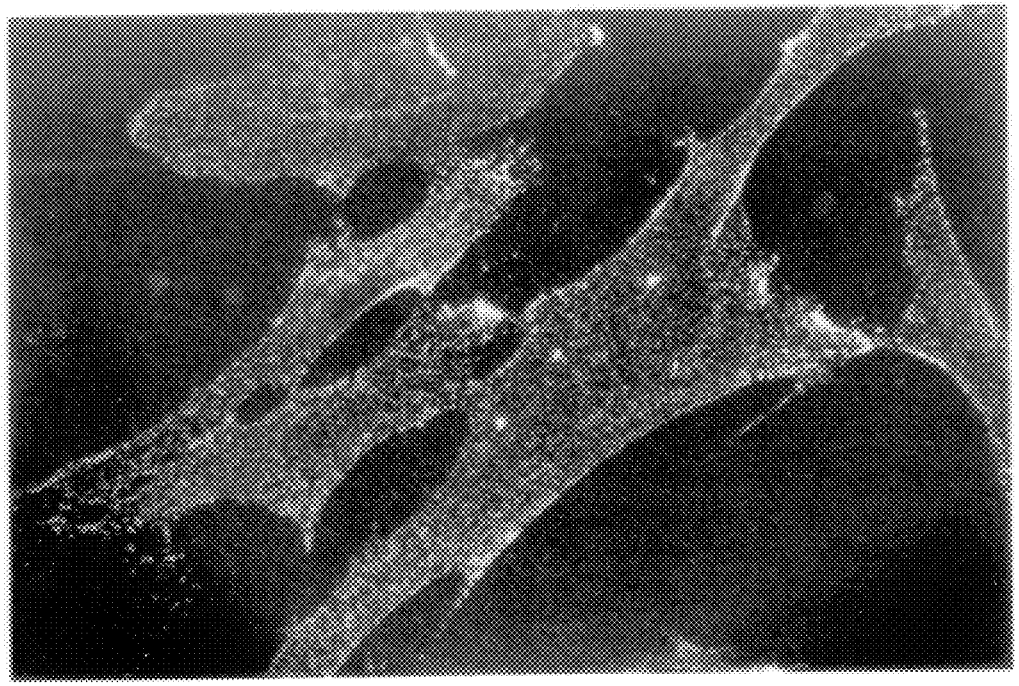
FIG. 10 SH-2 positive immuno-fluorescent image of the cells seen in FIG. 6. Magnification=400×.

The CD41 selected adherent cells were found to be SH-2 positive (such was verified by utilizing an antibody specific for SH-2 cell surface antigens, as described in the published U.S. Pat. No. 4,586,359. Cells derived from primary cultures of MSCs selected using the anti-CD41 antibody were grown onto glass cover slips and identified as MSCs by incubating the cells with SH-2 followed by fluorescin labeled secondary antibody. FIG. 9 shows the cells under bright field and FIG. 10 shows the fluorescent image. Immuno-reactivity to SH-2 was seen as a punctate pattern of fluorescence in the cells.

The above description of the invention is by way of illustration only. Other permutations and practices of the invention will be readily envisioned by one of ordinary skill in the art by view the above in conjunction with the appended drawings. Therefore, such permutations and variations are within the scope of the present invention.

What is claimed is:

1. A process for recovering human mesenchymal stem cells, comprising:

separating megakaryocytes from a human cell population that includes megakaryocytes and mesenchymal stem cells by use of an antibody for a surface antigen on the megakaryocytes, separated megakaryocytes having associated therewith human mesenchymal stem cells; and recovering human mesenchymal stem cells from the separated megakaryocytes.

2. The process of claim 1 wherein the human cell population comprises unfractionated human bone marrow.

3. The process of claim 1 wherein the human cell population comprises a fraction of human bone marrow that is enriched in megakaryocytes.

4. The process of claim 1 wherein said antibody is a $CD_{41}$ antibody.

5. A process for recovering human mesenchymal stem cells, comprising:

separating megakaryocytes from a human cell population that includes megakaryocytes and mesenchymal stem cells by use of an antibody for a surface antigen on the megakaryocytes, separated megakaryocytes having associated therewith mesenchymal stem cells; and culturing the separated megakaryocytes in a culture medium that favors the growth of mesenchymal stem cells.

6. The process of claim 5 wherein the human cell population comprises unfractionated bone marrow.

7. The process of claim 5 wherein the human cell population comprises a bone marrow fraction enriched for megakaryocytes.

8. The process of claim 5 wherein the antibody is a $CD_{41}$ antibody.

9. The process of claim 5 wherein the antibody is supported on magnetic beads.

10. A process for recovering human mesenchymal stem cells comprising:

recovering a cell population enriched for megakaryocytes from a human cell population including megakaryocytes and mesenchymal stem cells, said recovered cell population including megakaryocytes having mesenchymal stem cells associated therewith;

separating megakaryocytes from the recovered cell population, said separated megakaryocytes including megakaryocytes having mesenchymal stem cells associated therewith; and recovering human mesenchymal stem cells from the separated megakaryocytes.

11. The process of claim 10 wherein the cell population enriched for megakaryocytes is recovered by density cell separation.

12. The process of claim 10 wherein the human cell population comprises unfractionated bone marrow.

13. The process of claim 10 wherein the megakaryocytes are separated from the enriched cell population by use of an antibody for a surface antigen on the megakaryocytes.

14. The process of claim 13 wherein said antibody is a $CD_{41}$ antibody.

15. The process of claim 14 wherein the antibody is supported on magnetic beads.

* * * * *